United States Patent
Ashby et al.

(10) Patent No.: US 6,315,798 B1
(45) Date of Patent: Nov. 13, 2001

(54) PROSTHETIC IMPLANT ATTACHMENT SURFACE

(75) Inventors: Alan M. Ashby, Caen (FR); Declan P. Slemon, Limerick (IE); Melvin Schwartz, Jr., Point Pleasant, NJ (US)

(73) Assignee: Howmedica International S. De R.L. (IE)

( * ) Notice: Subject to any disclaimer, the term of this patent is extended or adjusted under 35 U.S.C. 154(b) by 0 days.

(21) Appl. No.: 09/399,208

(22) Filed: Sep. 17, 1999

Related U.S. Application Data

(62) Division of application No. 08/915,246, filed on Aug. 20, 1997, now Pat. No. 5,989,472, which is a continuation of application No. 08/536,286, filed on Sep. 29, 1995, now abandoned.

(30) Foreign Application Priority Data

Oct. 5, 1994 (GB) .................................................. 9420071

(51) Int. Cl.[7] ........................................................ A61F 2/38
(52) U.S. Cl. .................. 623/20.17; 623/20.2; 623/23.54; 623/23.5
(58) Field of Search ............................ 623/20, 18, 20.17, 623/20.2, 22.27, 22.23, 23.5, 23.51, 23.54, 23.59; 264/273, 250, 274

(56) References Cited

U.S. PATENT DOCUMENTS

| | | |
|---|---|---|
| 4,041,550 * | 8/1977 | Frazier . |
| 4,479,271 | 10/1984 | Bolesky et al. . |
| 4,924,583 | 5/1990 | Hummel et al. ........................ 29/460 |
| 4,955,911 * | 9/1990 | Frey et al. .............................. 623/16 |
| 4,978,355 * | 12/1990 | Frey et al. .............................. 623/16 |
| 4,997,445 | 3/1991 | Hodorek ................................. 623/16 |
| 5,019,104 * | 5/1991 | Whiteside et al. ..................... 623/20 |
| 5,108,435 | 4/1992 | Gustavson et al. .................... 623/16 |
| 5,181,924 * | 1/1993 | Gschwend et al. .................... 623/20 |

\* cited by examiner

*Primary Examiner*—Paul B. Prebilic
(74) *Attorney, Agent, or Firm*—Lerner, David, Littenberg, Krumholz & Mentlik, LLP

(57) ABSTRACT

A metal backing for inclusion in the manufacture of a prosthetic component having a plastic bearing element on an upper surface and has a bottom surface portion with elements for attachment to a bone. The backing has an upper surface portion at least part of which is formed by a grill element having exposed front and rear faces and which is intended to be embedded within the plastic bearing member during construction. The plastic bearing material of the bearing element can be molded so that all the faces thereof exposed to the grill are covered and the grill is embedded within the plastic material of the bearing element. The grill is located on a metal support and is provided with spacers on its front face to space the front face away from the support. The grill is cast integrally into the metal support during manufacture.

18 Claims, 2 Drawing Sheets

PROSTHETIC IMPLANT ATTACHMENT SURFACE

This application is a divisional of U.S. Ser. No. 08/915,246 filed Aug. 20, 1997, now U.S. Pat. No. 5,989,472 which is a continuation of U.S. application Ser. No. 08/536,286, filed Sep. 29, 1995 now abandoned.

BACKGROUND OF THE INVENTION

1. Field of the Invention

This invention relates to a metal backing for inclusion in the manufacture of a prosthetic component and to a metal component incorporating such a backing. More particularly it relates to a means of securing a synthetic plastic material such as polyethylene to a metal backing.

2. Description of the Prior Art

There are often difficulties in securing a metal backing to the synthetic plastic material of a bearing member, sometimes because of the limited space available.

Metal-backed patella components are well known within the industry. They have been subject to limitations on performance related to the small available space for their construction. Generally the factor affecting performance is the reliable and long term attachment of the plastic bearing elements to the metal backing which is used to provide the fixation surface of the device, either for cemented use or for biological ingrowth type applications. Traditional products have used riveting, snapping or molding techniques to provide for the interconnection of parts, these generally being geometric interference caused by this form of gross metal features on the metal backing, posts, holes, rims, etc.

U.S. Pat. No. 5,108,435 relates to an orthopedic implant having a cast mesh tissue ingrowth surface.

The present invention also has applications with regard to other metal backed components, for example, tibial components, elbow and shoulder components and hip cups.

SUMMARY OF THE INVENTION

According to the present invention a metal backing for inclusion in the manufacture of a prosthetic component which has a synthetic polymeric bearing element comprises a metallic element having a front portion with means for attachment to a bone and a rear portion at least part of which is formed by a grill having exposed front and rear faces and which is intended to be embedded within the bearing member during construction.

Thus, due to the construction of the metallic element, the synthetic plastic bearing material of the bearing element can be molded so that both exposed faces of the grill are covered and the grill is embedded within the synthetic plastics material bearing element.

Preferably the grill is located on a metal support and is provided with spacers on its front face to space said front face away from said support. The grill can be cast integrally into said metal support during manufacture.

In one preferred embodiment the front portion of the metal backing is provided with means for attachment to a bone with cement. In an alternative construction the metal backing can be provided with means for mechanical attachment to a bone. Thus, the front portion can be provided with a biological ingrowth surface to facilitate bone ingrowth.

With this arrangement the front portion of the metal backing can be provided with an intricate metal wire mesh and this mesh can be cast integrally into one side of a metal support on the other side of which said grill is located.

The invention also includes a prosthetic metal backed component including a metal backing set forth above and a synthetic plastics material bearing element having a rear bearing surface and a front portion within which the grill is embedded.

With this arrangement the grill is preferably molded integrally into the bearing element during manufacture. As mentioned above the invention is particularly, although not exclusively, applicable for use with a patella component.

The invention can be performed in various ways but one embodiment showing the application of the invention to a patella component will now be described by way of example and with reference to the accompanying drawings.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
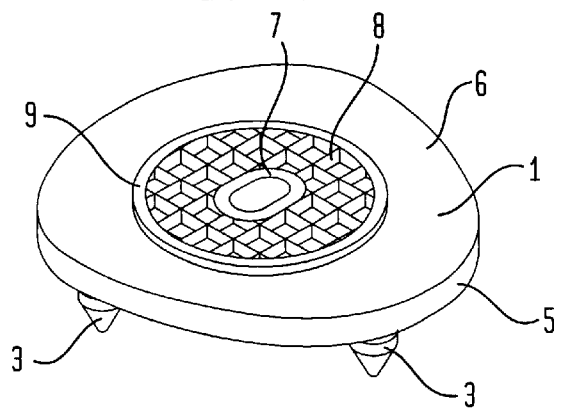
FIG. 1 is an isometric view of a metal backing for inclusion in the manufacture of a prosthetic patella component.
Figure 2:
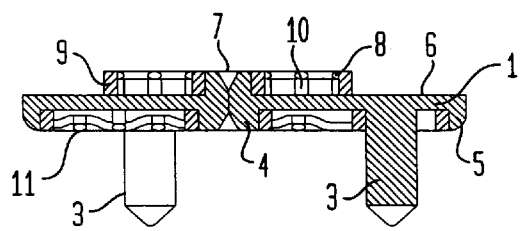
FIG. 2 is a cross-sectional side elevation through the component shown in FIG. 1.
Figure 3:
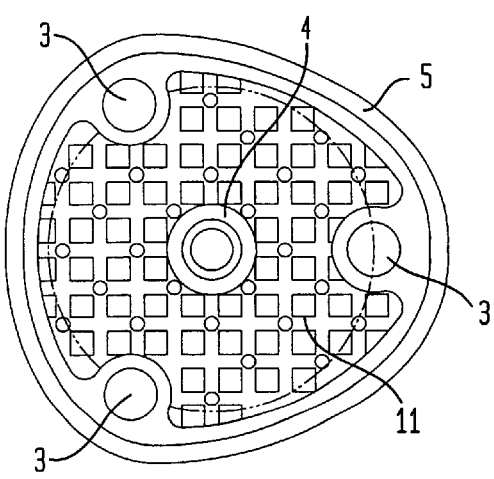
FIG. 3 is a plan view from beneath the component shown in FIGS. 1 and 2.
Figure 4:
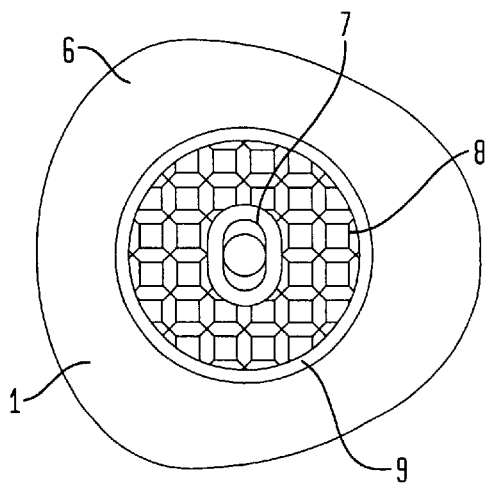
FIG. 4 is a plan view from above the same component.
Figure 5:
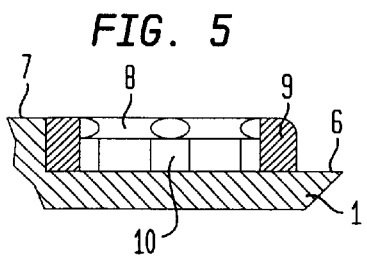
FIG. 5 is an enlarged cross-sectional view of a part of FIG. 2.
Figure 6:
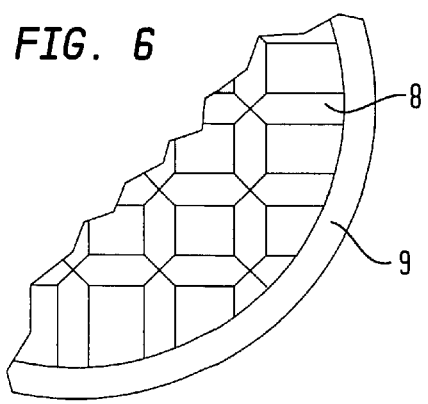
FIG. 6 is an enlarged part-plan view showing the grill.

FIGS. 1 to 7 show a metal backing for inclusion in the manufacture of a prosthetic patella component and comprises a shaped plate like metal support 1 on the front face of which is provided three location pins 3 and a central boss 4. On this face there is also a surrounding rim 5. The rear face 6 (top face of FIG. 2) is substantially flat apart from a projecting boss 7. Mounted on the boss 7 is a grill 8 having an outer rim 9. The grill is formed from substantially oval section members, best shown in FIG. 5, and is spaced away from the face 6 by integral supports (support posts) 10.

Figure 7:
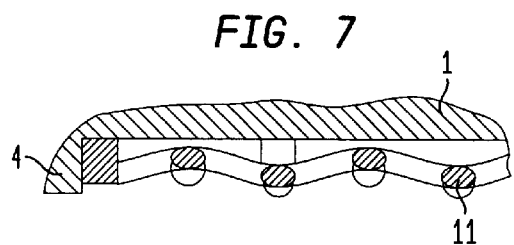
FIG. 7 is an enlarged part-cross-sectional elevation underside thereof of FIG. 2.

The space between the rim 5 on the front face and the boss is filled with a intricate metal mesh 11 as is most clearly shown in FIG. 7. The metal mesh 11 provides an ingrowth surface on the front face which is intended to be next to the prepared bone and the grill 8 is intended to be embedded in a synthetic plastic material bearing element to be described hereunder. The grill and wire mesh are preferably integrally cast with the metal support 1 using an investment casting technique where wax patterns for the castings are either assembled prior to casting, or ceramic inserts are used: Such a technique is taught in U.S. Pat. No. 5,108,435 the teachings of which are incorporated herein by reference.

Figure 8:
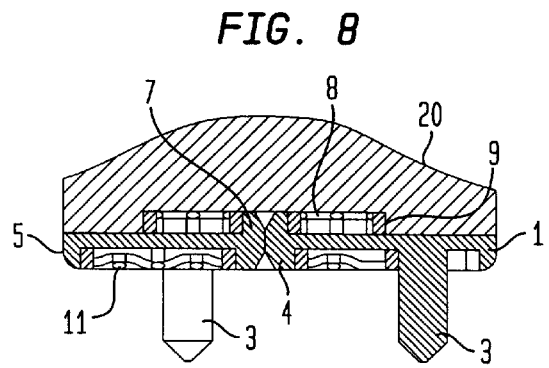
FIG. 8 is a cross-sectional side elevation of a complete prosthetic metal backed bearing component embodying the metal backing shown in FIGS. 1 to 7; and, FIG. 9 is a plan view of the component shown in FIG. 8.
Figure 9:
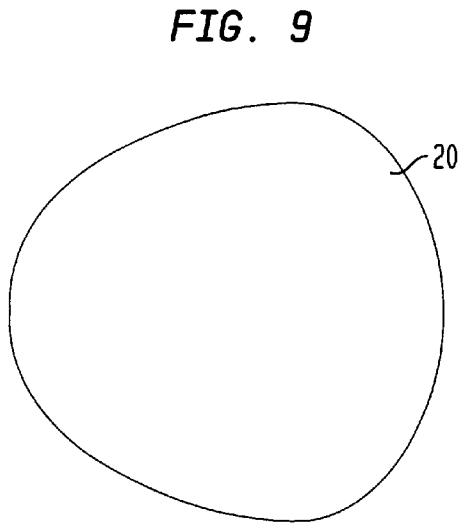

The metal backing is used with a synthetic plastic material (such as ultra high molecular-weight polyethylene) bearing element 20 as shown in FIG. 8. In plan view the bearing element 20 is substantially the same shape as the support 1.

Subsequent to the casting and finishing of the metal component, this component is then used as an insert within a plastic compression mold and polymer powder, for example, ultra-high molecular weight polyethylene (UHMWPE) bearing material is loaded on top of the backing plate and compression molded in place to yield the construction shown in FIG. 8. During this process the plastic material under the pressure and heat of the molding operation forms a continuous structure underneath the grill 8 thereby providing an excellent mechanical lock between the two parts.

Due to this construction it is possible to reduce the thickness of the metal structure so that a larger thickness of bearing plastic can be formed above it. This is in part because of the efficiency of the mechanical interlocking system but also because the grill construction reinforces the metal substrate of the component. A biological fixation surface in the opposite side of the component may be formed by the same general process, or by other techniques well known in the industry.

In the arrangement described, the metallic mesh 11 is intended to provide ingrowth, but if desired any suitable other surface could be used or a cement fixation surface can be applied in any manner well known in the art.

As described above, the invention is applied to a metal backed patella component but it can be used in other metal backed components, for example, tibial 25 components, elbow and shoulder components and hip cups where the ability to provide a rigid fixation in a restricted area will allow increased thickness of bearing material.

While several examples of the present invention have been described, it is obvious that many changes and modifications may be made thereunto, without departing from the spirit and scope of the invention.

We claim:

1. An orthopedic implant comprising: a metal backing having on one side a first metallic element integral therewith for attachment to a bone and on an opposite side a second metallic element integral therewith which is formed by a grill having front and rear faces spaced from said metal backing by support posts; and a molded polymeric bearing material on the second metallic element of the metal backing forming a continuous polymeric bearing structure on the metal backing and around the front and rear faces of the metal grill embedding the metal grill in the continuous polymeric structure, the continuous polymeric structure having the grill embedded therein includes the polymeric bearing surface which has generally the same shape as the metal backing.

2. The orthopedic implant as claimed in claim 1 in which said grill is provided with spacers on its first face to space said front face away from said metal backing.

3. The orthopedic implant as claimed in claim 2 in which said grill is cast integrally into said metal support during manufacture.

4. The orthopedic implant as claimed in claim 1 in which said first metallic element includes a grill member spaced from said metal backing.

5. The orthopedic implant as claimed in claim 4 in which said grill members are in the form of an intricate metal wire mesh.

6. The orthopedic implant as claimed in claim 5 in which each of said metal wire meshs are cast integrally onto said opposite side of said metal backing.

7. The orthopedic implant as claimed in claim 1 wherein said polymeric element has an outer bearing surface and an inner portion within which the grill is embedded.

8. The orthopedic implant as claimed in claim 7 in which said grill is molded integrally into said bearing element during manufacture.

9. An orthopedic implant element as claimed in claim 8 in which said orthopedic implant is a patella component.

10. A reinforced orthopedic implant having a polymeric bearing surface thereon, comprising;

a metal backing for an orthopedic implant having a front face and a rear face;

the front face of the metal backing being provided with location pins, a central boss, a peripheral rim and a metal mesh between the central boss and said peripheral rim, wherein the metal mesh is spaced away from the front face by support posts;

the rear face of the metal backing having a projecting boss, an outer rim and a metal grill between the projecting boss and outer rim, wherein the metal grill is spaced away from the rear surface by support posts; and a molded polymeric bearing material on the rear face of the metal backing forming a continuous polymeric structure on the rear face of the metal backing and underneath the metal grill embedding the metal grill in the continuous polymeric structure, the continuous polymeric structure having the metal grill embedded therein includes the polymeric bearing surface having substantially the same shape as the metal backing.

11. The orthopedic implant as claimed in claim 10 in which said grill is cast integrally into said metal support during manufacture.

12. The orthopedic implant as claimed in claim 10 in which said mesh on said front face is in the form of a metal grill member spaced from said metal backing.

13. The orthopedic implant as claimed in claim 12 in which said posts for spacing said metal grill members from said front and rear faces of said metal backing are integrated with said grill members and said metal backing.

14. The orthopedic implant as claimed in claim 12 in which said metal grill member, and said posts are cast integrally into said metal backing during manufacture.

15. The orthopedic implant as claimed in claim 12 in which said grill members on said front and rear face of said metal backing are in the form of an intricate metal wire mesh.

16. The orthopedic implant as claimed in claim 15 in which each of said metal grills are cast integrally onto said opposite sides of said metal backing.

17. The orthopedic implant as claimed in claim 12 in which said grill is molded integrally into said bearing element during manufacture.

18. The orthopedic implant as claimed in claim 10 in which said orthopedic implant is a patella component.

* * * * *

UNITED STATES PATENT AND TRADEMARK OFFICE
CERTIFICATE OF CORRECTION

PATENT NO. : 6,315,798 B1
DATED : November 13, 2001
INVENTOR(S) : Alan Ashby, Declan P. Slemon, and Melvin Schwartz It is certified that error appears in the above-identified patent and that said Letters Patent is hereby corrected as shown below:

Column 2,
Line 36, after "elevation" insert -- of the --.
Line 37, cancel "thereof".

Column 3,
Line 32, cancel "25".

Signed and Sealed this

Twenty-sixth Day of March, 2002

Attest:

JAMES E. ROGAN
Attesting Officer  Director of the United States Patent and Trademark Office